United States Patent [19]

Brown et al.

[11] Patent Number: 5,602,100

[45] Date of Patent: *Feb. 11, 1997

[54] DERMORPHIN ANALOGS HAVING PHARMACOLOGICAL ACTIVITY

[75] Inventors: William L. Brown, Laval; Peter W. Schiller, Montreal, both of Canada

[73] Assignee: Astra AB, Sodertalje, Sweden

[*] Notice: The portion of the term of this patent subsequent to May 16, 2011, has been disclaimed.

[21] Appl. No.: 238,038

[22] Filed: Apr. 21, 1994

Related U.S. Application Data

[63] Continuation-in-part of Ser. No. 374,521, Jun. 30, 1989, Pat. No. 5,312,899.

[30] Foreign Application Priority Data

Jun. 30, 1988 [CA] Canada ................................ 570874

[51] Int. Cl.$^6$ .................... A61K 38/00; A61K 38/02; C07K 5/00; C07K 7/00
[52] U.S. Cl. ............................................. 514/18; 530/330
[58] Field of Search ....................... 530/330, 331, 530/329; 514/17, 18

[56] References Cited

U.S. PATENT DOCUMENTS

| | | | |
|---|---|---|---|
| 4,320,051 | 3/1982 | Sarantakis | 260/112.5 |
| 4,350,627 | 9/1982 | de Castiglione et al. | 260/112.5 |
| 4,422,968 | 12/1983 | Haoli | 260/112.5 E |
| 4,428,938 | 1/1984 | Kisfaludy et al. | 424/177 |
| 4,657,892 | 4/1987 | Brantl | 514/16 |
| 5,312,899 | 5/1994 | Schiller | 530/331 |

FOREIGN PATENT DOCUMENTS

WO/8602079  4/1986  WIPO .............................. C07K 5/10

OTHER PUBLICATIONS

W. A. Banks and A. J. Kastin, "Peptides and the Blood-Brain Barrier: Lipophilicity as a Predictor of Permeability", *Brain Res. Bull.*, 15, pp. 287–292 (1985).
K. Chaki et al., "Comparison of the Antinociceptive Effects of New [D–Arg$^2$]–Dermorphin Tetrapeptide Analogs and Morphine in Mice", *Pharma. Biochem. & Behav.*, 31, pp. 439–444 (1988).
Y. C. Cheng and W. H. Prusoff, "Relationship Between the Inhibition Constant ($K_i$) and the Concentration of Inhibitor Which Causes 50 Percent Inhibition ($IC_{50}$) of an Enzymatic Reaction", *Biochem. Pharmacol.*, 22, pp. 3099–3102 (1973)*.
J. DiMaio et al., "Synthesis and Pharmaceutical Characterization In Vitro of Cyclic Enkephalin Analogues: Effect of Conformational Constraints on Opiate Receptor Selectivity", *J. Med. Chem.*, 25, pp. 1432–1438 (1982).
S. H. Ferreira and M. Nakamura, "Prostaglandin Hyperglasia: The Peripheral Analgesic Activity of Morphine, Enkephalins, and Opioid Antagonists", *Prostaglandins*, 18, pp. 191–200 (1979).

R. L. Follenfant et al., "Antinociceptive Effects of the Novel Opioid Peptide BW443C Compared with Classical Opiates; Peripheral Versus Central Actions", *Br. J. Pharmacol.*, 93, pp. 85–92 (1988).
G. W. Hardy et al., "Peripherally Acting Enkephalin Analogues. 1. Polar Pentapeptides", *J. Med. Chem.*, 31 pp. 960–966 (1988).
K. Kisara et al., "Dermorphin Analogues Containing D–Kyotorphin: Structure–Antinociceptive Relationships in Mice", *Br. J. Pharmacol.*, 87, p. 183 (1986).
M. G. Kris et al., "Control of Chemotherapy–Induced Diarrhea with the Synthetic Enkephalin BW942C: A Randomized Trial with Placebo in Patients Receiving Cisplatin", *J. Clin. Onc.*, 6, pp. 663–668 (1988).
F. M. Leslie, "Methods Used for the Study of Opioid Receptors", *Pharmacological Reviews*, 39, (1987)*.
J. A. H. Lord et al., "Endogenous Opioid Peptides: Multiple Agonists and Receptors", *Nature*, 267, pp. 495–499 (1977).
W. R. Martin et al., "The Effects of Morphine–and Nalorphine–Like Drugs in the Nondependent and Morphine Dependent Chronic Spinal Dog", *J. Pharmacol. Exp. Ther.*, 197, pp. 517–532 (1976).
J. Posner et al., "A Preliminary Study of the Pharmacokinetics of a Novel Enkephalin Analogue [Try–D–Arg–Gly–Phe (4NO$_2$)–Pro–NH$_2$ (BW443C)] in Healthy Volunteers", *Eur. J. Clin. Pharmacol.*, 34, pp. 67–71 (1988).
J. Rudinger, "Characteristics of the Amino Acids as Components of a Peptide Hormone Sequence" in *Peptide Hormones* (University Park Press, J. A. Parsons, ed., 1976).
N. J. W. Russell et al., "Opiates Inhibit the Discharges of Fine Afferent Units from Inflamed Knee Joint of the Cat", *Neuroscience Lett.*, 76, pp. 107–112 (1987).
T. Sato et al., "Opioid Activities of D–Arg$^2$ Substituted Tetrapeptides", *J. Pharmacol. Exp. Ther.*, 242(2), pp. 654–659 (1987).
P. W. Schiller et al., "Evidence for Topographical Analogy between Methionine–Enkephalin and Morphine Derivatives", *Biochemistry*, 16, pp. 1831–1838 (1977).
P. W. Schiller et al., "Unsulfated C–Terminal 7–Peptide of Cholecystokinin: A New Ligand of the Opiate Receptor", *Biochem. Biophys. Res. Commun.*, 85, pp. 1332–1338 (1978).
P. W. Schiller et al., "A Novel Cyclic Opioid Peptide Analog Showing High Preference for μ–Receptors", *Biochem and Biophys. Res. Commun.*, 127(2), pp. 558–564 (1985).

(List continued on next page.)

*Primary Examiner*—Avis M. Davenport
*Attorney, Agent, or Firm*—Fish & Neave; James F. Haley, Jr.; Andrew S. Marks

[57] ABSTRACT

This invention relates to novel dermorphin analogs having pharmacological activity. More particularly, this invention relates to novel tetrapeptides having specific structural features and a net charge of +2 or greater. The peptides of this invention are useful in treating pain and gastro-intestinal disorders. Accordingly, this invention also relates to pharmaceutical compositions comprising those peptides and methods for treating pain and gastro-intestinal disorders.

11 Claims, No Drawings

OTHER PUBLICATIONS

P. W. Schiller et al., "New Types of Opioid Peptide Analogs Showing High μ–Receptor Selectivity and Preference for Either Central or Peripheral Sites" in *Pept. Proc. Eur. Pept. Symp.,* 20th Meeting Sep. 4–9, 1988 (Walter de Gruyter & Co., G. Jung and E. Bayer, eds., 1989), pp. 613–615.

P. W. Schiller et al., "Dermophin Analogues Carrying an Increased Positive Net Charge in Their Message Domain Display Extremely High μ–Opioid Receptor Selectivity", *J. Med. Chem.,* 32, pp. 698–703 (1989).

P. W. Schiller et al., "Two New Families of Opioid Peptide Analogs Dispalying Extraordinary μ–Receptor Selectivity and Preference for Either Peripheral or Central Sites", *Advances in the Biosciences,* 75, pp. 85–88 (1989).

P. W. Schiller, "Development of Receptor–Specific Opioid Peptide Analogues", in *Progress in Medicinal Chemistry 28* (Elsevier Science Publishers B.V., G. P. Ellis et al. eds., 1991) pp. 301–340.

R. Schwyzer, "Molecular Mechanism of Opioid Receptor Selection", *Biochem.,* 25, pp. 6335–6342 (1986).

E. Siegmund et al., "A Method for Evaluating Both Non–Narcotic and Narcotic Analgesics", *Proc. Soc. Exp. Biol. Med.,* 95, pp. 729–731 (1957).

T. W. Smith et al., "Peripheral Antinociceptive Effects of N–Methyl Morphine", *Life Sci.,* 31, pp. 1205–1208 (1982).

C. Stein et al., "Antinociceptive Effects of μ and κ–Agonists in Inflammation are Enhanced by a Peripheral Opioid Receptor–Specific Mechanism", *Eur. J. Pharm.,* 155, pp. 255–264 (1988).

C. Stein et al., "Peripheral Opioid Receptors Mediating Antinociception in Inflammation Evidence for Involvement of μ, δ, and κ Receptors", *J. Phar. Exp. Ther.,* 248, pp. 1269–1275 (1989).

G. Woolfe and A. D. MacDonald, "The Evaluation of the Analgesic Action of Pethidine Hydrochloride (Demerol)", *J. Pharmacol. Exp. Ther.,* 80, pp. 300–307 (1944).

Schiller et al., *J. Med. Chem.,* vol. 32, 1989, pp. 698–703.

DERMORPHIN ANALOGS HAVING PHARMACOLOGICAL ACTIVITY

This application is a continuation-in-part of U.S. patent application Ser. No. 07/374,521, filed Jun. 30, 1989 and now U.S. Pat. No. 5,312,899.

TECHNICAL FIELD OF THE INVENTION

This invention relates to novel dermorphin analogs having pharmacological activity. More particularly, this invention relates to novel tetrapeptides having specific structural features and a net charge of +2 or greater. The peptides of this invention are useful in treating pain and gastro-intestinal disorders. Accordingly, this invention also relates to pharmaceutical compositions comprising those peptides and methods for treating pain and gastro-intestinal disorders.

BACKGROUND OF THE INVENTION

Dermorphin (H-Tyr-D-Ala-Phe-Gly-Tyr-Pro-Ser-NH$_2$) is an amphibian heptapeptide that possesses potent opioid-like activity in humans (T. Sato et al., *J. Pharmacol. Exp. Ther.*, 242, pp. 654–59 (1987)). Opioid peptides, such as dermorphin, bind with varying degrees of selectivity to peripherally- and centrally-located opioid receptors.

Three distinct categories of opioid receptors have been identified (designated μ, δ and κ) (W. Martin et al., *J. Pharmacol. Exp. Ther.*, 197, p. 517 (1977); J. Lord et al., *Nature*, 257, p. 495 (1977)). Although there is no definitive correlation between the binding of particular opioid receptors and specific opioid effects, it appears that the μ receptors predominantly mediate analgesic effects, while the δ and κ-receptors appear to mediate behavioral effects.

Lack of opioid receptor selectivity and access to the central nervous system has been linked to many dangerous side effects (such as physical dependence and respiratory depression). Conventional opiates (such as morphine, naloxone, levorphanol, enkephalin, endorphin and dynorphin) and analogs thereof are generally quite hydrophobic and are therefore, able to permeate lipid membranes, such as the blood-brain barrier. This permeability has been linked to CNS-related side effects, such as euphorea and addiction. In addition, conventional opiates typically are not highly selective for any particular type of opioid receptor. The side effects associated with the administration of opioid peptides and opioid peptide analogs have hindered their use as pharmacological agents.

In addition to undesired side effects, conventional opioid peptides tend to remain lodged in a patient's organs and fatty tissues. Such compounds must, therefore, be administered at high doses and are likely to cause toxic reactions associated with long term exposure to opiates.

Accordingly, there is a need for stable opioid peptide analogs that are potent analgesics. Such opioid peptide analogs should be highly μ-receptor selective, hydrophilic, peripherally-active and readily excreted from the body.

SUMMARY OF THE INVENTION

It is a principle objective of this invention to provide stable, dermorphin analogs which satisfy the above-mentioned criteria. The dermorphin analogs of this invention are tetrapeptides represented by Formula I:

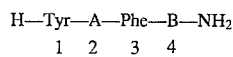

$$\text{H—Tyr—A—Phe—B—NH}_2 \quad (I)$$
$$\phantom{\text{H—}}1\phantom{\text{yr—}}2\phantom{\text{—Phe—}}3\phantom{\text{—B—}}4$$

wherein:

A is selected from the group consisting of D-α-amino acids;

B is selected from the group consisting of α-amino acids; and the overall net positive charge of the peptide is +2 or greater.

It is a further object of this invention to provide pharmaceutical compositions comprising one or more peptides of this invention and a pharmaceutically acceptable carrier or adjuvant.

It is also an object of this invention to provide methods for treating pain and gastro-intestinal disorders using the compounds and pharmaceutical compositions of this invention.

DETAILED DESCRIPTION OF THE INVENTION

In accordance with this invention, the following definitions apply:

The following abbreviations are used to designate the α-amino acids referred to herein:

A$_2$bu=α,γ-diaminobutyric acid
A$_2$pr=α,β-diaminopropionic acid
Ala=alanine
Arg=arginine
Gly=glycine
Hly=homolysine
Ile=isoleucine
Leu=leucine
Lys=lysine
Nle=norleucine
Nva=norvaline
Orn=ornithine
Phe=phenylalanine
Pro=proline
Ser=serine
Tyr=tyrosine
Val=valine The following abbreviations are used to designate certain chemical reagents and moieties referred to herein:

Boc=tert-butoxycarbonyl
BOP=benzotriazoyl-oxy-tris-dimethylaminophosphonium hexafluorophosphate
Cbz=carbobenzyloxy
CDI=N,N'-carbonyldiimidazole
DAGO=H-Tyr-D-Ala-Gly-MePhe-Gly-ol
DCC=N,N'-dicyclohexylcarbodiimide
DMAP=4-dimethylaminopyridine
DMF=N,N'-dimethylformamide
EEDQ=1-(ethyoxycarbonyl)-2-ethoxy-1,2-dihydroquinoline
Fmoc=9-fluorenylmethyloxycarbonyl
HF=hydrogen fluoride
HOBt=1-hydroxybenzotriazole
Mtr=4-methoxy-2,3,6-trimethylbenzenesulfonyl
TFA=trifluoroacetic acid
THF=tetrahydrofuran For ease of reference, the positions occupied by the α-amino acids in the peptides of this invention (i.e., the peptides of Formula I) will be designated "position (1)" through "position (4)", reading from N-terminus to C-terminus.

The term "α-amino acid" is used interchangeably with the term "amino acid" and refers to a chemical moiety having an amino terminus (N-terminus) and a carboxy or amide terminus (C-terminus) separated by a single carbon atom (referred to herein as the "m-carbon"). As used herein, the term "amino acid" or "α-amino acid" refers to either the free, unbound form, the form bound by a peptide bond at a single terminus (either the N- or the C-terminus) or the form bound at both the N- and the C-termini by peptide bonds.

The term "α-amino acid" encompasses all of the naturally occurring amino acids as well as modified natural α-amino acids such as homolysine, diaminobutyric acid, diaminopropionic acid, ornithine, norleucine and norvaline. Preferably, the α-amino acids used in this invention are selected from the group consisting of the naturally occurring α-amino acids and the following non-naturally occurring α-amino acids: homolysine, diaminobutyric acid, diaminopropionic acid, ornithine, norleucine and norvaline.

Unless expressly stated to the contrary, the amino acids used in this invention may be in the D- or L-configuration or any mixture thereof. Preferably, the amino acids used in the peptides of Formula I are amino acids, with the exception of the α-amino acid located in position (2). According to this invention, the α-amino acid in position (2) must be a D-α-amino acid.

The term "overall net positive charge" refers to the overall net positive charge of a peptide at physiological pH. Usually, the positive charge on the N-terminus of a peptide is offset by the negative charge of the terminal carboxy group. However, the peptides of this invention all have terminal amide bonds at their C-terminus. Accordingly, the positive charge on the N-terminus of the peptides of this invention is not offset by a negative charge on the C-terminus. For example, at least one positively charged α-amino acid must be present in the peptides of this invention in order for the peptide to have an overall net positive charge of +2 or greater. Examples of positively charged α-amino acids include lysine, arginine, ornithine, diaminobutyric acid and diaminopropionic acid.

The term "patient" refers to any mammal, including a human, that may be safely and effectively treated with the peptides and pharmaceutical compositions of this invention.

The term "pharmaceutically acceptable carrier or adjuvant" refers to a non-toxic carrier or adjuvant that may be administered to a patient, together with a peptide of this invention, and that does not destroy the pharmacological activity of that peptide.

The term "pharmaceutically effective amount" refers to an amount effective to alleviate pain or the symptoms of a gastrointestinal disorder in a patient.

The term "treating pain or gastro-intestinal disorders" refers to the alleviation of symptoms of pain or gastro-intestinal disorders.

The peptides of this invention are represented by Formula (I):

 (I)

wherein:

A is selected from the group consisting of D-α-amino acids;

B is selected from the group consisting of α-amino acids; and the overall net positive charge of the peptide is +2 or greater.

Preferred peptides of formula I are those wherein A is selected from the group consisting of D-Nva, D-Nle, D-Arg, D-Ala, D-Val, D-Ile, D-Leu, D-Ser, D-Phe and D-A$_2$bu; B is selected from the group consisting of Orn, A$_2$bu, Lys, Nva, Arg, A$_2$pr and Hly; and the overall net positive charge of the peptide is +2 or +3.

More preferably, A is selected from the group consisting of D-Nva, D-Nle and D-Arg; B is selected from the group consisting of Orn, A$_2$bu, Lys, A$_2$pr and Hly; and the overall net positive charge of the peptide is +2 or 3.

The preferred peptides of this invention have the following sequences:

H-Tyr-D-Nva-Phe-Orn-NH$_2$ BCH-752;

H-Tyr-D-Nle-Phe-Orn-NH$_2$ BCH-1763;

H-Tyr-D-Arg-Phe-A$_2$bu-NH$_2$ BCH-1764;

H-Tyr-D-Arg-Phe-Orn-NH$_2$ BCH-1765;

H-Tyr-D-Arg-Phe-Lys-NH$_2$ BCH-150;

H-Tyr-D-Arg-Phe-Arg-NH$_2$ BCH-1766;

H-Tyr-D-Arg-Phe-Nva-NH$_2$ BCH-1788;

H-Tyr-D-Ala-Phe-Lys-NH$_2$ BCH-1789;

H-Tyr-D-Nva-Phe-Lys-NH$_2$ BCH-2200;

H-Tyr-D-Ile-Phe-Lys-NH$_2$ BCH-2203;

H-Tyr-D-Nle-Phe-Lys-NH$_2$ BCH-2205;

H-Tyr-D-Val-Phe-Lys-NH$_2$ BCH-2206;

H-Tyr-D-Leu-Phe-Lys-NH$_2$ BCH-2207;

H-Tyr-D-Ser-Phe-Lys-NH$_2$ BCH-2209;

H-Tyr-D-Ala-Phe-Orn-NH$_2$ BCH-2219;

H-Tyr-D-Ile-Phe-Orn-NH$_2$ BCH-2456;

H-Tyr-D-Phe-Phe-Orn-NH$_2$ BCH-2457;

H-Tyr-D-Val-Phe-Orn-NH$_2$ BCH-2458;

H-Tyr-D-Leu-Phe-Orn-NH$_2$ BCH-2459;

H-Tyr-D-Phe-Phe-Lys-NH$_2$ BCH-2460;

H-Tyr-D-Ser-Phe-Orn-NH$_2$ BCH-2461;

H-Tyr-D-Phe-Phe-A$_2$bu-NH$_2$ BCH-2466;

H-Tyr-D-Val-Phe-A$_2$bu-NH$_2$ BCH-2467;

H-Tyr-D-Ile-Phe-A$_2$bu-NH$_2$ BCH-2468;

H-Tyr-D-Ser-Phe-A$_2$bu-NH$_2$ BCH-2469;

H-Tyr-D-Ala-Phe-A$_2$bu-NH$_2$ BCH-2470;

H-Tyr-D-Nva-Phe-A$_2$bu-NH$_2$ BCH-2471;

H-Tyr-D-Nle-Phe-A$_2$bu-NH$_2$ BCH-2472;

H-Tyr-D-Leu-Phe-A$_2$bu-NH$_2$ BCH-2474;

H-Tyr-D-A$_2$bu-Phe-Orn-NH$_2$ BCH-2580;

H-Tyr-D-Arg-Phe-Ser-NH$_2$ BCH-2688; and

H-Tyr-D-Arg-Phe-Ala-NH$_2$ BCH-2689.

More preferred peptides of this invention have the following sequences:

H-Tyr-D-Arg-Phe-Nva-NH$_2$ BCH-1788;

H-Tyr-D-Ala-Phe-Lys-NH$_2$ BCH-1789;

H-Tyr-D-Nle-Phe-Lys-NH$_2$ BCH-2205;

H-Tyr-D-Val-Phe-Lys-NH$_2$ BCH-2206;

H-Tyr-D-Leu-Phe-Lys-NH$_2$ BCH-2207;

H-Tyr-D-Ser-Phe-Lys-NH$_2$ BCH-2209;

H-Tyr-D-Phe-Phe-Orn-NH$_2$ BCH-2457; and

H-Tyr-D-Val-Phe-Orn-NH$_2$ BCH-2458.

The most preferred peptide of this invention has the following sequence:

H-Tyr-D-Arg-Phe-Nva-NH$_2$ BCH-1788.

The peptides of this invention are useful for the treatment of pain and gastro-intestinal disorders. Without wishing to be bound by theory, the peptides of this invention possess the appropriate structural and conformational features to bind the µ-receptor and therefore, show high µ-receptor selectivity. As discussed above, selective binding of the µ-receptor has been linked to the analgesic activity of opiates.

The peptides of this invention possess a high overall net positive charge, which, to a significant degree, prevents them from crossing the blood-brain barrier. The peptides of this invention, therefore, tend to bind selectively to peripherally-located µ-receptors. Accordingly, the administration of the peptides of this invention is not accompanied by many of the centrally-mediated side effects and addictive potential of conventional opiates and opioid peptide analogs.

The high overall net positive charge possessed by the peptides of this invention decreases the lipophilicity of those peptides. This decreased lipophilicity allows the peptides of this invention to be more readily absorbed in aqueous fluids than conventional opioid peptides and opioid peptide analogs, which show only marginal solubility in aqueous media. This increased hydrophilicity allows the peptides of this invention to be administered in aqueous dosage forms (such as an aqueous injectable liquid) and be more readily and effectively cleared from the body.

In addition, the increased charge of the peptides of this invention may increase µ-receptor affinity and concurrently, decrease δ-receptor affinity. Such a change in affinity would result in greater µ-receptor selectivity.

Augmenting the positive charge of the peptide of this invention from +1 to +2 or greater generally results in higher µ-receptor affinity. The receptor binding profiles of these peptides are consistent with the membrane compartment concept discussed in Schwyzer, *Biochemistry*, 25, p. 6336 (1986). According to that theory, the heightened µ-receptor affinity may be due to the increased accumulation of peptides carrying a high positive charge in the anionic fixed-charge compartment of the membrane, where µ-receptors are located. The decrease in δ-receptor affinity may be due to increasing electrostatic repulsion in the positively charged aqueous compartment, which contains δ-receptors.

The presence of a D-α-amino acid at position (2) in the peptides of this invention makes these peptides especially well-suited for use in the treatment of gastro-intestinal disorders, such as diarrhea. Without wishing to be bound by theory, D-α-amino acids are more resistant to degradation by proteases found in the digestive tract. Accordingly, the peptides of this invention are able to withstand the harsh environment of the digestive tract due to their enhanced stability to proteolytic degradation. In addition to their heightened stability, the peptides of this invention are effective at lower doses than conventional opiates and opioid peptide analogs. We believe that these peptides resist being absorbed into the digestive lining of the stomach and intestines because of their decreased affinity for lipid tissues. These peptides are therefore more potent than conventional opiates and opioid analogs at a given dosage level under similar physiological conditions.

The peptides of this invention may be easily and conveniently prepared using any conventional peptide production methodologies. Such methods are described in detail in co-pending U.S. patent application Ser. No. 07/374,521, filed Jun. 30, 1989, the entire disclosure of which is hereby incorporated herein by reference.

The peptides of this invention may be prepared, for example, by conventional solid phase or solution phase reactions. In a typical solution phase reaction, an appropriately protected amino acid is coupled with a second appropriately protected amino acid in the presence of a suitable peptide coupling agent (such as DCC, CDI, EEDQ and BOP). The solvent should be a polar, aprotic organic solvent (such as THF, DMF, dichloromethane, chloroform and diethyl ether). A catalyst (such as DMAP, copper (II) chloride and HOBt) may be used. The coupling reaction is repeated until all of the desired residues have been linked. A suitable deprotection method may then be employed to remove any remaining protecting groups.

Alternatively, the peptides of this invention may be prepared by the Merrifield solid phase synthetic method. A Merrifield resin is prepared by well-known techniques. A covalently attached and appropriately protected α-amino acid residue or nascent peptide may be attached to the resin by its C- or N-terminus. Sequential treatment of the resin with appropriately protected amino acids affords the desired peptide chain.

Once the desired peptide is assembled, the peptide may be freed from the resin according to well-known protocols. One common and preferred method employs liquid HF. However, where the peptide requires selective removal of certain protecting groups (such as a Boc-protected amino terminus), suitable reaction conditions must be used. Boc may be selectively removed from an amino functionality using, for example, cold TFA at 0° C. at a pH of between 8 and 9. The resultant TFA salt can then be exposed to mild aqueous base treatment to yield a free amino group. Reactions for selectively removing other protecting groups, such as Cbz and Fmoc, are also well known.

Preferably, the peptides of this invention are prepared by standard solid-phase techniques on a p-methylbenzhydrylamine resin, using Boc- or Fmoc-protected α-amino acid derivatives and DCC as the coupling reagent. This reaction is preferably carried out at atmospheric pressure, at a temperature of between about −10° C. and 25° C., with stirring, for a period of between about 4 and 6 hours. Dichloromethane or DMF is the preferred solvent.

Once the desired peptide has been prepared, it may be isolated and purified using any conventional technique. Preferred techniques, alone or in any combination, include: crystallization, chromatography, extraction and electrophoresis. Preferred chromatographic techniques include normal phase HPLC, reversed phase HPLC, ion exchange, affinity and gel permeation chromatography. Gel filtration followed by reversed phase chromatography is especially preferred.

The amounts of reactants and specific reaction conditions utilized in the above-mentioned reactions may vary. In general, stoichiometric amounts of each of the reactants are usually employed and the reactant concentrations are typically held at 0.1M. In practice, the specific amounts of reactants used will vary depending on the reaction conditions and the nature of the reactants.

The present invention provides pharmaceutical compositions comprising a pharmaceutically effective amount of the peptides of this invention, or pharmaceutically acceptable salts thereof, and a pharmaceutically acceptable carrier or adjuvant. Such compositions may be in any conventional form including tablets, capsules, caplets, powders, granules, lozenges, suppositories, reconstitutable powders or liquid preparations (such as oral or sterile parenteral solutions or suspensions).

Pharmaceutically acceptable salts of the peptides of this invention may be formed by reaction with an appropriate acid. Preferred acids include hydrochloric, hydrobromic, phosphoric, acetic, fumaric, salicylic, citric, lactic, mandelic, tartaric, oxalic and methanesulfonic acid.

For consistent administration, preferred pharmaceutical compositions of this invention are in the form of a unit dose. The unit dose for oral administration may be in the form of tablets and capsules and may contain conventional expedients. For example, binding agents (such as acacia, gelatin, sorbitol and polyvinylpyrrolidone), fillers (such as lactose, sugar, maize-starch, calcium phosphate, sorbitol or glycine), tabletting lubricants (such as magnesium stearate), disintegrants (such as starch, polyvinylpyrrolidone, sodium starch glycolate and microcrystalline cellulose) and wetting agents (such as lauryl sulphate) may be used.

Solid oral compositions may be prepared by conventional methods, including blending, filling and tabletting. Repeated blending operations may be used to distribute the active ingredient throughout compositions that contain large quantities of fillers. Tablets may be coated according to methods well-known in pharmaceutical practice, including enteric coating.

Liquid oral compositions may be prepared in any conventional form, including emulsions, syrups and elixirs. Alternatively, the composition may be presented as a dry product for reconstitution with water or other suitable vehicle before use. For example, the following vehicles may be used: suspending agents (such as sorbitol, syrup, methyl cellulose, gelatin, hydroxyethylcellulose, carboxymethylcellulose, aluminum stearate gel and hydrogenated edible fats), emulsifying agents (such as sorbitan monooleate and acacia), non-aqueous vehicles (such as edible oils (including almond oil and fractionated coconut oil, oily esters), oily esters, glycerine, propylene glycol, ethylene glycol and ethyl alcohol), preservatives (such as ethyl parahydroxybenzoate, n-propyl parahydroxybenzoate, n-butyl parahydroxybenzoate and sorbic acid), conventional flavoring agents and coloring agents.

For parenteral administration, fluid unit dosage forms may be prepared by utilizing the peptide and a sterile vehicle. Depending on the concentration used, the peptides of this invention may be either suspended or dissolved in the vehicle. In preparing solutions, the peptides of this invention may advantageously be dissolved in water. Adjuvants (such as a local anaesthetic, preservative or buffering agent) may also be suspended or dissolved in the vehicle prior to use. Stability of the suspension or solution may be enhanced by freeze drying. A surfactant or wetting solution may be added to the suspension or solution to facilitate uniform distribution of the peptide.

Typical pharmaceutical compositions of this invention contain from about 0.1% to about 99% by weight, and preferably between about 10% and about 60% by weight, of a peptide of this invention. As the skilled artisan will appreciate, the exact percentage of active ingredient will vary depending upon several factors, including the precise administration method.

The present invention also provides methods for treating pain or gastro-intestinal disorders in a patient comprising the step of administering to the patient a pharmaceutically effective amount of a pharmaceutical composition described herein.

The dosage of the peptide used in the methods of this invention will vary, depending on factors such as the weight of the patient, the potency of the peptide and the judgement of the treating physician. Suitable single unit dosages for a human are typically between about 0.01 mg and about 100 mg, preferably between about 0.2 mg and about 50 mg. Typically, the total daily dose of active peptide should be between about 0.01 mg and about 10 mg/kg body weight. A course of therapy can range from a single administration to multiple administrations over an extended period of several weeks. Multiple administrations may be carried out intermittently or continuously, until the patient's symptoms are alleviated.

In order that this invention be more clearly understood, the following examples are set forth. These examples are for the purposes of illustration only, and are not to be construed as limiting the scope of this invention in any manner.

EXAMPLES

Example 1

GENERAL METHODS

Precoated plates (silica gel G, 250 μm, Analtech. Newark, Del.) were used for ascending TLC in the following solvent systems (v/v): (1) n-BuOH/AcOH/H$_2$O (BAW) (4:1:5, organic phase) and (2) n-BuOH/pyridine/AcOH/H$_2$O (BPAW) (15:10:3:12). Reversed-phase HPLC was performed on a Varian VISTA 5500 liquid chromatograph, utilizing a Waters column (30×0.78 cm) pached with C-18 Bondpak reversed-phase (10 μm) material.

For amino acid analyses, each peptide (0.2 mg) was hydrolyzed in dearerated tubes with 6N HCl (0.5 mL) containing a small amount of phenol for 24 hours at 110° C. Hydrolysates were analyzed on a Beckman model 121C amino acid analyzer equipped with a model 126 Data System integrator.

Example 2

PEPTIDE SYNTHESIS

Amino acid derivatives were purchased from IAF Biochem International (Laval, Quebec). Both Boc and Fmoc amino acids were used for the preparation of the various peptides. Side chain protection was as follows: (1) Boc amino acids: tosyl (Arg), benzyl-oxycarbonyl (Orn), 2-chlorobenzyloxycarbonyl (Lys), Boc (Tyr); and (2) Fmoc amino acids: Boc A$_2$bu), Mtr (D-Arg).

All peptides were prepared by the manual solid phase technique, using p-methylbenzhydrylamine resin (1% cross-linked, 100–200 mesh, 0.38 meq/g titratable amino) obtained from IAF Biochem International (Laval, Quebec). Specific reaction protocols have been published in Schiller et al., *Biochemistry*, 16, p. 1831 (1977) and are also contained in co-pending U.S. patent application Ser. No. 07/374,521 (incorporated herein by reference). Using these techniques, the following peptides were prepared:

H-Tyr-D-Nva-Phe-Orn-NH$_2$ BCH-752;
H-Tyr-D-Nle-Phe-Orn-NH$_2$ BCH-1763;
H-Tyr-D-Arg-Phe-A$_2$bu-NH$_2$ BCH-1764;
H-Tyr-D-Arg-Phe-Orn-NH$_2$ BCH-1765;
H-Tyr-D-Arg-Phe-Lys-NH$_2$ BCH-150;
H-Tyr-D-Arg-Phe-Arg-NH$_2$ BCH-1766;
H-Tyr-D-Arg-Phe-Nva-NH$_2$ BCH-1788;
H-Tyr-D-Ala-Phe-Lys-NH$_2$ BCH-1789;
H-Tyr-D-Nva-Phe-Lys-NH$_2$ BCH-2200;
H-Tyr-D-Ile-Phe-Lys-NH$_2$ BCH-2203;
H-Tyr-D-Nle-Phe-Lys-NH$_2$ BCH-2205;
H-Tyr-D-Val-Phe-Lys-NH$_2$ BCH-2206;
H-Tyr-D-Leu-Phe-Lys-NH$_2$ BCH-2207;
H-Tyr-D-Ser-Phe-Lys-NH$_2$ BCH-2209;
H-Tyr-D-Ala-Phe-Orn-NH$_2$ BCH-2219;
H-Tyr-D-Ile-Phe-Orn-NH$_2$ BCH-2456;
H-Tyr-D-Phe-Phe-Orn-NH$_2$ BCH-2457;
H-Tyr-D-Val-Phe-Orn-NH$_2$ BCH-2458;
H-Tyr-D-Leu-Phe-Orn-NH$_2$ BCH-2459;

-continued

H-Tyr-D-Phe-Phe-Lys-NH$_2$ BCH-2460;
H-Tyr-D-Ser-Phe-Orn-NH$_2$ BCH-2461;
H-Tyr-D-Phe-Phe-A$_2$bu-NH$_2$ BCH-2466;
H-Tyr-D-Val-Phe-A$_2$bu-NH$_2$ BCH-2467;
H-Tyr-D-Ile-Phe-A$_2$bu-NH$_2$ BCH-2468;
H-Tyr-D-Ser-Phe-A$_2$bu-NH$_2$ BCH-2469;
H-Tyr-D-Ala-Phe-A$_2$bu-NH$_2$ BCH-2470;
H-Tyr-D-Nva-Phe-A$_2$bu-NH$_2$ BCH-2471;
H-Tyr-D-Nle-Phe-A$_2$bu-NH$_2$ BCH-2472;
H-Tyr-D-Leu-Phe-A$_2$bu-NH$_2$ BCH-2474;
H-Tyr-D-A$_2$bu-Phe-Orn-NH$_2$ BCH-2580;
H-Tyr-D-Arg-Phe-Ser-NH$_2$ BCH-2688; and
H-Tyr-D-Arg-Phe-Ala-NH$_2$ BCH-2689.

Example 3

PEPTIDE PURIFICATION

All peptides were purified by gel filtration on a Sephadex-G25 column in 0.5N AcOH, followed by reversed-phase chromatography on an octadecasilyl silica column, using a linear gradient of 0–80% MeOH in 1% TFA. When further purification was necessary, purification to homogeneity was performed by semipreparative reversed-phase HPLC (20–50% MeOH; linear gradient in 0.1% TFA). Final products were obtained as lyophilisates. Homogeneity was established by TLC and HPLC. All peptides were at least 95% pure, as determined by HPLC.

Example 4

BINDING ASSAY

An opioid receptor binding assay was conducted using representative demorphin analogs of this invention. The binding affinities of the tested peptides for both the μ- and the δ-receptors were determined.

Receptor binding studies with rat brain membrane preparations were performed as reported in Schiller et al., Biochem. Biophys. Res. Commun., 85, p. 1322 (1978). [$^3$H] DAGO and [$^3$H]DSLET at respective concentrations of 0.72 and 0.78 nM were used as radioligands. Incubations were performed at 0° C. for 2 hours. The opioid receptor binding affinities of the tested peptides for the μ- and the δ-receptors—$K_i^\mu$ and $K_i^\delta$, respectively—were determined by monitoring the displacement of the radioligands from the rat brain membrane preparations. Peptides having a ratio $K_i^\mu/K_i^\delta > 1.0$ bind selectively to the μ-opioid receptor. [Leu$^5$]enkephalin, an endogenous opiate peptide with preference for the δ-opioid receptor, was used as a control.

IC50 values were determined from log dose-displacement curves. $K_i$ values were calculated from the obtained IC50 values using the equation of Cheng and Prusoff (see Y. C. Cheng and W. H. Prusoff, "Relationship Between the Inhibition Constant ($K_i$) and the Concentration of Inhibitor Which Causes 50 Percent Inhibition ($I_{50}$) of an Enzymatic Reaction", Biochem. Pharmacol., 22, pp. 3099–3102 (1973)). Dissociation constants of [$^3$H]DAGO and [$^3$H] DSLET were 1.3 and 2.6 nM, respectively. The results are reported in Table 1.

TABLE 1

Binding Assay of Dermorphin Analogs[a]

| Compound | [$^3$H] DAGO $K_i^\mu$ | [$^3$H] HSLET $K_i^\delta$ | $K_i^\delta/K_i^\mu$ |
|---|---|---|---|
| H-Tyr-D-Nva-Phe-Orn-NH$_2$ | 1.17 ± 0.28 | 2200 ± 630 | 1880 |
| H-Tyr-D-Nle-Phe-Orn-NH$_2$ | 1.35 ± 0.19 | 2870 ± 30 | 2130 |
| H-Tyr-D-Arg-Phe-A$_2$bu-NH$_2$ | 5.78 ± 0.53 | 12600 ± 4,100 | 2180 |
| H-Tyr-D-Arg-Phe-Orn-NH$_2$ | 1.20 ± 0.26 | 9290 ± 1,300 | 7740 |
| H-Tyr-D-Arg-Phe-Lys-NH$_2$ | 1.69 ± 0.25 | 19200 ± 2000 | 11400 |
| H-Tyr-D-Ala-Gly-Phe(NMe)-Gly-ol (DAGO) | 1.22 ± 0.12 | 1280 ± 90 | 1050 |
| Leu-enkephalin | 9.43 ± 2.07 | 2.53 ± 0.35 | 0.27 |
| H-Tyr-D-Arg-Phe-Arg-NH$_2$ | 98.8 ± 24.5 | 12000 ± 1200 | 121 |
| H-Tyr-D-Arg-Phe-Nva-NH$_2$ | 11.7 ± 2.8 | >2530 | >216 |
| H-Tyr-D-Ala-Phe-Lys-NH$_2$ | 33.3 ± 2.7 | 4430 | 133 |
| H-Tyr-D-Nva-Phe-Lys-NH$_2$ | 2.27 ± 0.06 | >2530 | >1110 |
| H-Tyr-D-Ile-Phe-Lys-NH$_2$ | 7.49 ± 0.71 | >2530 | >338 |
| H-Tyr-D-Nle-Phe-Lys-NH$_2$ | 12.4 ± 3.7 | 3800 | 306 |
| H-Tyr-D-Val-Phe-Lys-NH$_2$ | 6.58 ± 0.97 | >2530 | >384 |
| H-Tyr-D-Leu-Phe-Lys-NH$_2$ | 168 ± 15 | >2530 | >15 |
| H-Tyr-D-Ser-Phe-Lys-NH$_2$ | 24.1 ± 2.8 | >2530 | >105 |
| H-Tyr-D-Ala-Phe-Orn-NH$_2$ | 10.68 ± 2.54 | 9878.00 ± 691.50 | 924.51 |
| H-Tyr-D-Ile-Phe-Orn-NH$_2$ | 4.49 ± 1.15 | 4276.67 ± 139.67 | 952.35 |
| H-Tyr-D-Phe-Phe-Orn-NH$_2$ | 7.39 ± 3.58 | 2464.00 ± 92.50 | 333.37 |
| H-Tyr-D-Val-Phe-Orn-NH$_2$ | 13.34 ± 4.79 | 8781.67 ± 1141.20 | 658.27 |
| H-Tyr-D-Leu-Phe-Orn-NH$_2$ | 77.49 ± 20.58 | 18606.0 ± 1416.18 | 240.10 |
| H-Tyr-D-Phe-Phe-Lys-NH$_2$ | 19.01 ± 4.97 | 1900 ± 171.30 | 99.47 |
| H-Tyr-D-Ser-Phe-Orn-NH$_2$ | 13.17 ± 3.68 | 15942.3 ± 2426.94 | 1210.57 |
| H-Tyr-D-Phe-Phe-A$_2$bu-NH$_2$ | 2.81 ± 0.79 | 1424.67 ± 133.08 | 507.59 |
| H-Tyr-D-Val-Phe-A$_2$bu-NH$_2$ | 2.64 ± 1.68 | 6278.00 ± 1363.14 | 1113.55 |
| H-Tyr-D-Ile-Phe-A$_2$bu-NH$_2$ | 9.70 ± 1.55 | 2526.67 ± 130.55 | 260.61 |
| H-Tyr-D-Ser-Phe-A$_2$bu-NH$_2$ | 5.11 ± 1.52 | 5475.67 ± 109.18 | 1071.20 |
| H-Tyr-D-Ala-Phe-A$_2$bu-NH$_2$ | 5.91 ± 0.94 | 3728.33 ± 254.63 | 630.58 |
| H-Tyr-D-Nva-Phe-A$_2$bu-NH$_2$ | 0.56 ± 0.13 | 441.00 ± 14.11 | 790.51 |
| H-Tyr-D-Nle-Phe-A$_2$bu-NH$_2$ | 10.23 ± 2.42 | 2126.33 ± 83.59 | 207.88 |
| H-Tyr-D-Leu-Phe-A$_2$bu-NH$_2$ | 69.82 ± 21.38 | 13055.0 ± 932.99 | 186.98 |
| H-Tyr-D-A$_2$bu-Phe-Orn-NH$_2$ | 9.28 ± 2.72 | 3821.67 ± 549.17 | 411.98 |

[a]Mean of three determinations ± SEM

Each and every one of the tested dermorphin analogs of this invention bound selectively to the μ-opioid receptor. This impressive and consistent selectivity is primarily due to the high overall net positive charge of +2 or greater. This theory can be evidenced by comparing the results of H-Tyr-D-Nva-Phe-Orn-NH$_2$, a dermorphin analog of this invention having an overall net positive charge of +2, with an analogous peptide having only a +1 charge, H-Tyr-D-Nva-Phe-Asn-NH$_2$. H-Tyr-D-Nva-Phe-Asp-NH$_2$ had only moderate μ-receptor selectivity (K$_i^\mu$/K$_i^\delta$=37.3). That peptide displayed a ten-fold decrease in μ-receptor affinity and a five-fold increase in δ-receptor affinity, compared with its +2-charged counterpart, H-Tyr-D-Nva-Phe-Orn-NH$_2$. H-Tyr-D-Nva-Phe-Orn-NH$_2$ showed superior μ-receptor selectivity (K$_i^\mu$/K$_i^\delta$=1880). Thus, the increase in overall net positive charge from +1 to +2 or greater in structurally similar peptides results in greater μ-receptor selectivity.

Example 5

BIOASSAYS

Opioid activity was determined by measuring the ability of a given peptide to inhibit electrically-induced contractions of guinea pig ileum (GPI) and mouse vas deferens (MVD). The GPI and MVD bioassays were carried out as reported in Schiller et al. (supra) and DiMaio et al., *J. Med. Chem.*, 25, p. 1432 (1982). A log dose-response curve was determined with [Leu$^5$]enkephalin ("leu -enkephalin") as a control for each GPI and MVD preparation.

μ- versus δ-receptor selectivity

Activity in the GPI assay is predictive of the μ-receptor interactions while activity in the MVD assay indicates δ-receptor interactions. Accordingly, a IC50(MVD)/IC50(GPI) ratio of >1 indicates a preference for binding the μ-receptor over the δ-receptor. The results obtained are described in Table 2.

Each and every one of the tested dermorphin analogs had IC50(MVD)/IC50(GPI) >1, indicating μ-selectivity. The results qualitatively agree with the receptor binding assays reported in Example 4. Quantitatively, however, the IC50(MVD)/IC50(GPI) ratios were lower than what would have been predicted, given the corresponding results in the binding assays. This discrepancy may be caused by the fact that the GPI assay is not as reliable as the binding assay for the determination of μ receptors since it is also influenced by κ and δ receptors. Therefore, this test serves only as a qualitative prediction for μ selectivity.

μ- versus κ-receptor Selectivity

κ-receptor interactions were determined by measuring K$_e$ values for naloxone as an antagonist in the GPI assay. High K$_e$ values (in the range of 20–30 nM) are associated with κ-receptor interactions. Low K$_e$ values (in the range of 1–2 nM) are associated with μ-receptor interactions. K$_e$ values for naloxone were determined from the ratio of IC50 values obtained in the presence of and in the absence of a fixed naloxone concentration. The IC50 values of the tested compounds were normalized according to published procedure (F. M. Leslie, "Methods Used for the Study of Opioid Receptors", *Pharmacological Reviews*, 39 (1987)). The results obtained are described in Table 3.

TABLE 3

K$_e$ Values (Naloxone) of Positively Charged Opioid Peptide Analogs in the Guinea Pig Ileum Assay[a]

| Compound | Ke (nm) |
| --- | --- |
| H-Tyr-D-Nva-Phe-Orn-NH$_2$ (BCH-752) | 1.55 ± 0.23 |
| H-Tyr-D-Nle-Phe-Orn-NH$_2$ (BCH-1763) | 1.01 ± 0.18 |
| H-Tyr-D-Arg-Phe-A$_2$bu-NH$_2$ (BCH-1764) | 1.32 ± 0.05 |
| H-Tyr-D-Arg-Phe-Orn-NH$_2$ (BCH-1765) | 1.24 ± 0.12 |
| H-Tyr-D-Arg-Phe-Lys-NH$_2$ (BCH-150) | 1.17 ± 0.08 |
| H-Tyr-D-Ala-Gly-Phe-(NMe)-Gly-ol (DAGO) | 0.800 ± 0.100 |
| Leu-enkephalin | 1.53 ± 0.43 |

[a]Mean of three determinations ± SEM

The low K$_e$ values displayed by the dermorphin analogs of this invention are indicative of μ-receptor interactions and rule out additional interactions with κ-receptors. Considered with the GPI/MVD results reported above, this test indicates that the synthetic dermorphin analogs of this invention specifically and selectively bind the μ-opioid receptor.

Example 6

PHARMACOLOGICAL ASSAYS

Two in vivo pharmacological assays were conducted to determine the analgesic effects of the peptides of this invention: the mouse writhing test and the mouse hot plate test.

Mouse Writhing Test (PBQ)

The mouse writhing test detects both peripherally and centrally mediated analgesic effects. The test procedure is described in Siegmund et al., *Proc. Soc. Exp. Biol. Med.*, 95, p. 729 (1957). In this test, a control group of albino mice was injected intraperitoneally with 0.3 ml/20 g body weight of a 0.02% solution of 2-phenyl-1,4-benzoquinone (PBQ). The writhing and contortional movements of the mice over the following 15 minutes were recorded. A second group of mice was given a dose of a synthetic dermorphin analog according to this invention, then allowed to wait a period of Guinea Pig Ileum (GPI) and Mouse Vas Deferens (MVD) Assay of Opioid Peptide Analogs[a]

| | GPI | | MVD | | MVD/GPI ratio |
| --- | --- | --- | --- | --- | --- |
| | IC$_{50}$ (nM) | relative potency | IC$_{50}$ (nM) | relative potency | IC$_{50}$ |
| H-Tyr-D-Nva-Phe-Orn-NH$_2$ | 104 ± 15 | 2.36 ± 0.33 | 271 ± 63 | 0.0420 ± 0.0098 | 2.61 |
| H-Tyr-D-Nle-Phe-Orn-NH$_2$ | 168 ± 33 | 1.46 ± 0.29 | 2290 ± 270 | 0.00498 ± 0.00058 | 13.6 |
| H-Tyr-D-Arg-Phe-A$_2$bu-NH$_2$ | 257 ± 56 | 0.956 ± 0.208 | 659 ± 123 | 0.0173 ± 0.0032 | 2.56 |
| H-Tyr-D-Arg-Phe-Orn-NH$_2$ | 346 ± 121 | 0.712 ± 0.249 | 1090 ± 279 | 0.0105 ± 0.0027 | 3.15 |
| H-Tyr-D-Arg-Phe-Lys-NH$_2$ | 338 ± 41 | 0.728 ± 0.089 | 781 ± 146 | 0.0146 ± 0.0027 | 2.31 |
| H-Tyr-D-Ala-Gly-Phe(NMe)-Gly-ol (DAGO) | 28 ± 3.7 | 8.69 ± 1.14 | 950 ± 269 | 0.0120 ± 0.0034 | 33.6 |
| Leu-enkephalin | 246 ± 39 | 1 | 11.4 ± 1.1 | 1 | 0.0463 |

[a]Mean of three determinations ± SEM time before being administered the PBQ injection. The average number of writhes was then recorded and compared to the control group. The results of this test are expressed as the dosage of peptide that reduces the number of writhes by 50% at a given time interval (referred to as ED50).

The results of these experiments are displayed in Table 4.

The results of Table 4 indicate increased antinociceptive activity. The potency of each of the tested peptides was equal to or better than morphine in a similar assay (R. Follenfacnt et al., *Br. J. Pharmacol.*, 93, p. 85 (1988)).

TABLE 4

Inhibitory Effect on PBQ-Induced Writhing

| Compound | PBQ (20 min.) ED$_{50}$ (mg/Kg) |
| --- | --- |
| H-Tyr-D-Nva-Phe-Orn-NH$_2$ | 0.2 |
| H-Tyr-D-Nle-Phe-Orn-NH$_2$ | 0.3 |
| H-Tyr-D-Arg-Phe-A$_2$bu-NH$_2$ | 0.13 |
| H-Tyr-D-Arg-Phe-Orn-NH$_2$ | <1 |
| H-Tyr-D-Arg-Phe-Lys-NH$_2$ | 0.65 |
| H-Tyr-D-Arg-Phe-Nva-NH$_2$ | 1.3 |
| H-Tyr-D-Ala-Phe-Lys-NH$_2$ | 0.6 |
| H-Tyr-D-Nva-Phe-Lys-NH$_2$ | 0.3 |
| H-Tyr-D-Ile-Phe-Lys-NH$_2$ | 0.8 |
| H-Tyr-D-Nle-Phe-Lys-NH$_2$ | 1.8 |
| H-Tyr-D-Val-Phe-Lys-NH$_2$ | 4.8 |
| H-Tyr-D-Leu-Phe-Lys-NH$_2$ | 0 9 |
| H-Tyr-D-Ser-Phe-Lys-NH$_2$ | 2.8 |
| H-Tyr-D-Ala-Phe-Orn-NH$_2$ | ~1 |
| H-Tyr-D-Ile-Phe-Orn-NH$_2$ | 0.6 |
| H-Tyr-D-Phe-Phe-Orn-NH$_2$ | 1.8 |
| H-Tyr-D-Val-Phe-Orn-NH$_2$ | 1.0 |
| H-Tyr-D-Leu-Phe-Orn-NH$_2$ | 0 10 |
| H-Tyr-D-Phe-Phe-Lys-NH$_2$ | ~3 |
| H-Tyr-D-Ser-Phe-Orn-NH$_2$ | 0.7 |
| H-Tyr-D-Phe-Phe-A$_2$bu-NH$_2$ | 0.2 |
| H-Tyr-D-Val-Phe-A$_2$bu-NH$_2$ | 2 |
| H-Tyr-D-Ile-Phe-A$_2$bu-NH$_2$ | 3–10 |
| H-Tyr-D-Ser-Phe-A$_2$bu-NH$_2$ | 1.5 |
| H-Tyr-D-Ala-Phe-A$_2$bu-NH$_2$ | 0.3 |
| H-Tyr-D-Nva-Phe-A$_2$bu-NH$_2$ | 0.2 |
| H-Tyr-D-Nle-Phe-A$_2$bu-NH$_2$ | 0.8 |
| H-Tyr-D-Leu-Phe-A$_2$bu-NH$_2$ | >10 |
| H-Tyr-D-A$_2$bu-Phe-Orn-NH$_2$ | 1.2 |
| morphine | 0.6 |

A variation of the mouse writhing experiment was also conducted to determine peripheral versus central binding preferences of certain peptides of this invention. In this experiment, 10 mg/kg of N-methyllevallorphan (NML), a known peripheral opioid antagonist, was administered to the mice before injection of the synthetic dermorphin peptide. A reversal of the analgesic effects of the synthetic dermorphin peptide (demonstrated by an increase in ED50) indicates that the peptide prefers to bind peripherally-located, rather than centrally-located, opioid receptors.

The antinociceptive effects of H-Tyr-D-Arg-Phe-Lys-NH$_2$, H-Tyr-D-Nva-Phe-Lys-NH$_2$ and H-Tyr-D-Nva-Phe-Orn-NH$_2$ were partially or totally antagonized by prior administration of NML. Centrally-active opiates such as morphine are not antagonized by NML. These results demonstrate that the synthetic dermorphin analogs of this invention, to a great extent, selectively bind peripherally-located μ-opioid receptors.

In addition to the mouse writhing data, respiratory depression was measured in certain treated mice. Respiratory depression is a commonly observed side effect characteristic of centrally-acting opiates. These reulsts are expressed in Table 5.

TABLE 5

Rat Respiration Rate

| BCH # | SEQUENCE | Dose mg/kg | Breaths per min. |
| --- | --- | --- | --- |
| | morphine (reference) | 30 | 104 ± 6 |
| | Control | 0 | 142 ± 5 |
| 150 | H-Tyr-D-Arg-Phe-Lys-NH$_2$ | 30 | 121 ± 6 |
| 1763 | H-Tyr-D-Nle-Phe-Orn-NH$_2$ | 30 | 162 ± 10 |
| 752 | H-Tyr-D-Nva-Phe-Orn-NH$_2$ | 30 | 122 ± 14 |
| 1788 | H-Tyr-D-Arg-Phe-Nva-NH$_2$ | 30 | 163 ± 9 |
| 1788 | H-Tyr-D-Arg-Phe-Nva-NH$_2$ | 100 | 125 ± 4 |
| 1789 | H-Tyr-D-Ala-Phe-Lys-NH$_2$ | 30 | 182 ± 24 |
| 2205 | H-Tyr-D-Nle-Phe-Lys-NH$_2$ | 30 | 158 ± 7 |
| 2205 | H-Tyr-D-Nle-Phe-Lys-NH$_2$ | 100 | 150 ± 4 |
| 2206 | H-Tyr-D-Val-Phe-Lys-NH$_2$ | 30 | 168 ± 13 |

The lack of effect of most of the compounds of the invention on respiratory despression is noticeable when compared to morphine.

Mouse Hot Plate Test

The mouse hot plate test is an assay which only detects centrally-mediated analgesic effects. This test was carried out using the protocol described in G. Woolfe and A. MacDonald, *J. Pharmacol. Exp. Ther.*, 80, p. 300 (1984). The results are displayed in Table 6 below:

TABLE 6

Inhibitory Effect On Hot Plate Stimulus

| BCH # | SEQUENCE | Dose (mg/kg) | Time (min.) | % of animals showing a 50% increase |
| --- | --- | --- | --- | --- |
| | morphine (reference) | ED$_{50}$ = 2.7 | | |
| 150 | H-Tyr-D-Arg-Phe-Lys-NH$_2$ | ED$_{50}$ = 19 | | |
| 752 | H-Tyr-D-Nva-Phe-Orn-NH$_2$ | ED$_{50}$ = 5.2 | | |
| 1763 | H-Tyr-D-Nle-Phe-Orn-NH$_2$ | 40 | 120 | 90 |
| 1764 | H-Tyr-D-Arg-Phe-A$_2$bu-NH$_2$ | 40 | 60 | 100 |
| 1765 | H-Tyr-D-Arg-Phe-Orn-NH$_2$ | 40 | 120 | 100 |
| 1766 | H-Tyr-D-Arg-Phe-Arg-NH$_2$ | — | — | — |
| 1788 | H-Tyr-D-Arg-Phe-Nva-NH$_2$ | 40 | 60 | 45 |
| 1788 | H-Tyr-D-Arg-Phe-Nva-NH$_2$ | 100 | 60 | 60 |
| 1789 | H-Tyr-D-Ala-Phe-Lys-NH$_2$ | 40 | 120 | 40 |
| 1789 | H-Tyr-D-Ala-Phe-Lys-NH$_2$ | 100 | 60 | 80 |
| 2200 | H-Tyr-D-Nva-Phe-Lys-NH$_2$ | — | — | — |
| 2203 | H-Tyr-D-Ile-Phe-Lys-NH$_2$ | 40 | 120 | 80 |
| 2205 | H-Tyr-D-Nle-Phe-Lys-NH$_2$ | 40 | 30 | 60 |
| 2205 | H-Tyr-D-Nle-Phe-Lys-NH$_2$ | 100 | 60 | 60 |
| 2206 | H-Tyr-D-Val-Phe-Lys-NH$_2$ | 40 | 120 | 30 |
| 2206 | H-Tyr-D-Val-Phe-Lys-NH$_2$ | 100 | 120 | 90 |
| 2207 | H-Tyr-D-Leu-Phe-Lys-NH$_2$ | 40 | 30 | 20 |
| 2207 | H-Tyr-D-Leu-Phe-Lys-NH$_2$ | 100 | 50 | 0 |
| 2209 | H-Tyr-D-Ser-Phe-Lys-NH$_2$ | 40 | 30 | 40 |
| 2209 | H-Tyr-D-Ser-Phe-Lys-NH$_2$ | 100 | 30 | 40 |
| 2219 | H-Tyr-D-Ala-Phe-Orn-NH$_2$ | 40 | 30 | 60 |
| 2456 | H-Tyr-D-Ile-Phe-Orn-NH$_2$ | 40 | 60 | 40 |
| 2456 | H-Tyr-D-Ile-Phe-Orn-NH$_2$ | 100 | 60 | 50 |
| 2457 | H-Tyr-D-Phe-Phe-Orn-NH$_2$ | 40 | 60 | 40 |
| 2458 | H-Tyr-D-Val-Phe-Orn-NH$_2$ | 40 | 30 | 30 |
| 2458 | H-Tyr-D-Val-Phe-Orn-NH$_2$ | 100 | 60 | 55 |
| 2459 | H-Tyr-D-Leu-Phe-Orn-NH$_2$ | — | — | — |
| 2460 | H-Tyr-D-Phe-Phe-Lys-NH$_2$ | — | — | — |
| 2461 | H-Tyr-D-Ser-Phe-Orn-NH$_2$ | 40 | 30 | 50 |
| 2466 | H-Tyr-D-Phe-Phe-A$_2$bu-NH$_2$ | 40 | 60 | 80 |
| 2467 | H-Tyr-D-Val-Phe-A$_2$bu-NH$_2$ | 40 | 60 | 90 |

TABLE 6-continued

Inhibitory Effect On Hot Plate Stimulus

| BCH # | SEQUENCE | Dose (mg/kg) | Time (min.) | % of animals showing a 50% increase |
|---|---|---|---|---|
| 2468 | H-Tyr-D-Ile-Phe-A$_2$bu-NH$_2$ | — | — | — |
| 2469 | H-Tyr-D-Ser-Phe-A$_2$bu-NH$_2$ | 40 | 60 | 90 |
| 2470 | H-Tyr-D-Ala-Phe-A$_2$bu-NH$_2$ | 40 | 120 | 90 |
| 2471 | H-Tyr-D-Nva-Phe-A$_2$bu-NH$_2$ | 40 | 60 | 100 |
| 2472 | H-Tyr-D-Nle-Phe-A$_2$bu-NH$_2$ | 40 | 60 | 60 |
| 2474 | H-Tyr-D-Leu-Phe-A$_2$bu-NH$_2$ | — | — | — |
| 2580 | H-Tyr-D-Abu-Phe-Orn-NH$_2$ | 40 | 60 | 80 |
| 2687 | H-Tyr-D-Arg-Phe-Phe-NH$_2$ | 40 | 60 | 70 |
| 2688 | H-Tyr-D-Arg-Phe-Ser-NH$_2$ | 40 | 60 | 100 |
| 2689 | H-Tyr-D-Arg-Phe-Ala-NH$_2$ | — | — | — |

Since most of the peptides of the invention were not potent centrally, it was impossible to determine an ED$_{50}$ value. Therefore, the results are expressed as the % of mice that demonstrated a 50% increase in time before responding to the hot plate. A result is considered insignificant if 30% of mice or lower have responded.

As can be seen from Table 6, the doses required to obtain a response are very high for most of the compounds of the invention, indicating very low centrally-mediated effects. One way to quantitate this effect is to measure the ratio of ED$_{50}$ for PBQ assay over ED$_{50}$ for the hot plate assay. This ratio is 4.5 for morphine; 29.2 for BCH-150; and 26 for BCH-752, indicating a strong peripheral/central activity ratio for the compounds of the invention.

I claim:

1. A peptide of formula I:

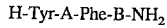

H-Tyr-A-Phe-B-NH$_2$      (I)

wherein:

A is selected from the group consisting of D-α-amino acids;

B is selected from the group consisting of α-amino acids; and the overall net positive charge of the peptide is +2 or greater.

2. The peptide according to claim 1, wherein:

A is selected from the group consisting of D-Nva, D-Nle, D-Arg, D-Ala, D-Val, D-Ile, D-Leu, D-Ser, D-Phe and D-A$_2$bu;

B is selected from the group consisting of Orn, A$_2$bu, Lys, Nva, Arg, A$_2$pr and Hly; and and the overall net positive charge of the peptide is +2 or +3.

3. The peptide according to claim 2, wherein:

A is selected from the group consisting of D-Nva, D-Nle and D-Arg; and

B is selected from the group consisting of Orn, A$_2$bu, Lys, A$_2$pr and Hly.

4. The peptide according to claim 1 selected from the group consisting of:

H-Tyr-D-Arg-Phe-Orn-NH$_2$;
H-Tyr-D-Arg-Phe-Arg-NH$_2$;
H-Tyr-D-Arg-Phe-Nva-NH$_2$;
H-Tyr-D-Ala-Phe-Lys-NH$_2$;
H-Tyr-D-Nva-Phe-Lys-NH$_2$;
H-Tyr-D-Ile-Phe-Lys-NH$_2$;
H-Tyr-D-Nle-Phe-Lys-NH$_2$;
H-Tyr-D-Val-Phe-Lys-NH$_2$;
H-Tyr-D-Leu-Phe-Lys-NH$_2$;
H-Tyr-D-Ser-Phe-Lys-NH$_2$;
H-Tyr-D-Ala-Phe-Orn-NH$_2$;
H-Tyr-D-Ile-Phe-Orn-NH$_2$;
H-Tyr-D-Phe-Phe-Orn-NH$_2$;
H-Tyr-D-Val-Phe-Orn-NH$_2$;
H-Tyr-D-Leu-Phe-Orn-NH$_2$;
H-Tyr-D-Phe-Phe-Lys-NH$_2$;
H-Tyr-D-Ser-Phe-Orn-NH$_2$;
H-Tyr-D-Phe-Phe-A$_2$bu-NH$_2$;
H-Tyr-D-Val-Phe-A$_2$bu-NH$_2$;
H-Tyr-D-Ile-Phe-A$_2$bu-NH$_2$;
H-Tyr-D-Ser-Phe-A$_2$bu-NH$_2$;
H-Tyr-D-Ala-Phe-A$_2$bu-NH$_2$;
H-Tyr-D-Nva-Phe-A$_2$bu-NH$_2$;
H-Tyr-D-Nle-Phe-A$_2$bu-NH$_2$;
H-Tyr-D-Leu-Phe-A$_2$bu-NH$_2$;
H-Tyr-D-A$_2$bu-Phe-Orn-NH$_2$;
H-Tyr-D-Arg-Phe-Ser-NH$_2$; and
H-Tyr-D-Arg-Phe-Ala-NH$_2$.

5. The peptide according to claim 4, selected from the group consisting of:

H-Tyr-D-Arg-Phe-Nva-NH$_2$;
H-Tyr-D-Ala-Phe-Lys-NH$_2$;
H-Tyr-D-Nle-Phe-Lys-NH$_2$;
H-Tyr-D-Val-Phe-Lys-NH$_2$;
H-Tyr-D-Leu-Phe-Lys-NH$_2$;
H-Tyr-D-Ser-Phe-Lys-NH$_2$;
H-Tyr-D-Phe-Phe-Orn-NH$_2$; and
H-Tyr-D-Val-Phe-Orn-NH$_2$.

6. A pharmaceutical composition comprising the peptide according to any one of claims 1–5 and a pharmaceutically acceptable carrier or adjuvant.

7. A pharmaceutical composition according to claim 6, wherein the peptide is present in an amount effective for the treatment of pain.

8. A pharmaceutical composition according to claim 6, wherein the peptide is present in an amount therapeutically effective for the treatment of gastro-intestinal disorders by selective binding to peripherally located opioid μ-receptors.

9. The pharmaceutical composition according to claim 8, wherein the gastro-intestinal disorder is diarrhea.

10. A method for treating pain in a patient comprising the step of administering to the patient a pharmaceutically effective amount of the pharmaceutical composition according to any one of claims 6 or 7.

11. A method for treating gastro-intestinal disorders by selective binding to peripherally located opioid μ-receptors in a patient comprising the step of administering to the patient a pharmaceutically effective amount of the pharmaceutical composition according to any one of the claims 6, 8 or 9.

* * * * *